United States Patent
Tseng et al.

(10) Patent No.: US 11,204,419 B2
(45) Date of Patent: Dec. 21, 2021

(54) METHOD AND RADAR OF LIFE DETECTION

(71) Applicant: Sil Radar Technology Inc., Kaohsiung (TW)

(72) Inventors: Yi-Ting Tseng, Kaohsiung (TW); Fu-Kang Wang, Kaohsiung (TW); Sheng-You Tian, Kaohsiung (TW)

(73) Assignee: Sil Radar Technology Inc., Kaohsiung (TW)

( * ) Notice: Subject to any disclaimer, the term of this patent is extended or adjusted under 35 U.S.C. 154(b) by 372 days.

(21) Appl. No.: 16/431,851

(22) Filed: Jun. 5, 2019

(65) Prior Publication Data
US 2020/0158858 A1  May 21, 2020

(30) Foreign Application Priority Data
Nov. 16, 2018  (TW) .................................. 107140892

(51) Int. Cl.
*G01S 13/88*  (2006.01)
*G01S 7/41*  (2006.01)
(Continued)

(52) U.S. Cl.
CPC ............ *G01S 13/887* (2013.01); *G01S 7/415* (2013.01); *G01S 13/888* (2013.01);
(Continued)

(58) Field of Classification Search
CPC ....... A61B 5/0507; A61B 5/05; A61B 5/0004; A61B 5/02444; G01S 13/88; G01S 7/415;
(Continued)

(56) References Cited

U.S. PATENT DOCUMENTS 9,603,555 B2 *  3/2017  Horng ................... A61B 5/0816
9,952,722 B2 *  4/2018  Chang ................... G06F 1/3262
(Continued)

FOREIGN PATENT DOCUMENTS

CA  2718699 A1 *  9/2009  ............. G01S 13/08
CN  103919527 A     7/2014
(Continued)

OTHER PUBLICATIONS

Tzyy-Sheng Horng, Self-Injection-Locked Radar: an Advance in Continuous-Wave Technology for Emerging Radar Systems, 2013 Asia-Pacific Microwave Conference Proceedings, pp. 566-569. (Year: 2013).*
(Continued)

*Primary Examiner* — Olumide Ajibade Akonai
(74) *Attorney, Agent, or Firm* — Demian K. Jackson; Jackson IPG PLLC

(57) ABSTRACT

In a life detection method of the present invention, a signal transceiver is configured to transmit a transmission signal to an area and receive a reflected signal from the area as a detection signal, a demodulator coupled to the signal transceiver is configured to receive and demodulate the detection signal to output a demodulated signal, a compute element coupled to the demodulator is configured to receive the demodulated signal and compute a RMS value of the demodulated signal, and a determination element coupled to the compute element is configured to receive the RMS value of the demodulated signal and determine whether having a living body within the area according to the RMS value and a RMS threshold value.

10 Claims, 4 Drawing Sheets

(51) Int. Cl.
*A61B 5/024* (2006.01)
*A61B 5/0507* (2021.01)
*G01S 7/35* (2006.01)
*A61B 5/05* (2021.01)
*G01S 13/56* (2006.01)

(52) U.S. Cl.
CPC ............. *A61B 5/02438* (2013.01); *A61B 5/05* (2013.01); *A61B 5/0507* (2013.01); *G01S 7/352* (2013.01); *G01S 13/56* (2013.01)

(58) Field of Classification Search
CPC ........ G01S 13/536; G01S 7/352; G01S 13/32; G01S 7/35; G01S 13/003; G01S 13/888; G01S 13/584; G01S 13/56; G01S 13/887
See application file for complete search history.

(56) References Cited

U.S. PATENT DOCUMENTS

| | | | |
|---|---|---|---|
| 2011/0102234 A1 | 5/2011 | Adams et al. |
| 2013/0234729 A1 | 9/2013 | Jau et al. |
| 2016/0307418 A1 | 10/2016 | Pantus et al. |
| 2018/0083358 A1 | 3/2018 | Wang et al. |
| 2018/0235481 A1 | 8/2018 | Liu et al. |

FOREIGN PATENT DOCUMENTS

| | | |
|---|---|---|
| CN | 104142499 A | 11/2014 |
| CN | 106054156 A | 10/2016 |
| CN | 106405542 A | 2/2017 |
| CN | 106821347 A | 6/2017 |
| CN | 108761450 A | 11/2018 |

OTHER PUBLICATIONS

Fu-Kang Wang et al, Chest-Worn Health Monitor Based on Bistatic Self-Injection-Locked Radar, IEEE Transactions on Biomedical Engineering, vol. 62, No. 12, Dec. 2015, pp. 2931-2940. (Year: 2015).*
Fu-Kang Wang et al, Seeing Through Walls with a Self-Injection-Locked Radar to detect hidden people, 2012 IEEE/MTT-S International Microwave Symposium Digest, pp. 1-3. (Year: 2012).*
Li et al., A review on recent progress of portable short-range noncontact microwave radar systems, IEEE Transactions on Microwave Theory and Techniques, May 2017, vol. 65, No. 5, pp. 1692-1706 (Year: 2017).*
Taiwanese Office Action dated Apr. 19, 2019 for Taiwanese Patent Application No. 107140892, 7 pages.
Pin-Hsun Juan et al., SIL-Radar-based Rat Detector for Warehouse Management System, IMBioC 2019, May 6-8, 2019.
Chinese Office Action dated Aug. 3, 2021 for Chinese Patent Application No. 201811591714.9, 16 pages.

* cited by examiner

METHOD AND RADAR OF LIFE DETECTION

FIELD OF THE INVENTION

This invention generally relates to a detection method, and more particularly to a life detection method.

BACKGROUND OF THE INVENTION

Rats concealed in boxes and transported with freight may cause problems, such as disease spreading and food contamination, so that rodent detection is necessary for disease control during transporting goods. Ultrasonic microphone may be applied to recognize rodents due to frequency band of rodent is between 20 kHz and 110 kHz. Alternatively, thermal imaging camera also may be utilized to track rodents concealed in covered boxes. However, detection range of ultrasonic microphone or thermal imaging camera is limited because of poor penetration to obstacles.

SUMMARY

The object of the present invention is to detect whether there is a living body within an area by wireless RF signals. Large area detection is available because wireless RF signals have the ability of penetrating non-metallic objects.

A life detection method of the present invention comprises following steps: transmitting a transmission signal to an area and receiving a reflected signal from the area as a detection signal by using a signal transceiver; receiving and demodulating the detection signal to output a demodulated signal by using a demodulator coupled to the signal transceiver; receiving the demodulated signal and computing a RMS value of the demodulated signal by using a compute element coupled to the demodulator; and receiving the RMS value of the demodulated signal and determining whether having a living body within the area according to the RMS value and a RMS threshold value by using a determination element coupled to the compute element.

A life detection radar of the present invention comprises a signal transceiver, a demodulator and a signal processor. The signal transceiver includes a self-injection-locked oscillator and an antenna element. The antenna element is coupled to the self-injection-locked oscillator and configured to receive an oscillation signal, transmit the oscillation signal to an area as a transmission signal and receive a reflected signal from the area as a detection signal. The detection signal is configured to be injected into the self-injection-locked oscillator such that the self-injection-locked oscillator operates in a self-injection-locked state. The demodulator is electrically connected to the signal transceiver and configured to receive and demodulate the oscillation signal as a demodulated signal. The signal processor is electrically connected to the demodulator and configured to receive the demodulated signal. The signal processor includes a compute element and a determination element, the compute element is configured to compute a RMS value of the demodulated signal, the determination element is coupled to the compute element and configured to receive the RMS value and determine whether having a living body within the area according to the RMS value and a RMS threshold value.

The present invention utilizes the compute element to compute the RMS value of the demodulated signal and utilizes the determination element to determine whether having a living body within the area according to the RMS value and a RMS threshold value. Rapid life detection is possible because wireless signals penetrative through to goods are provided to detect living body and the computation process is not complex in the present invention.

DETAILED DESCRIPTION OF THE INVENTION

Figure 1:
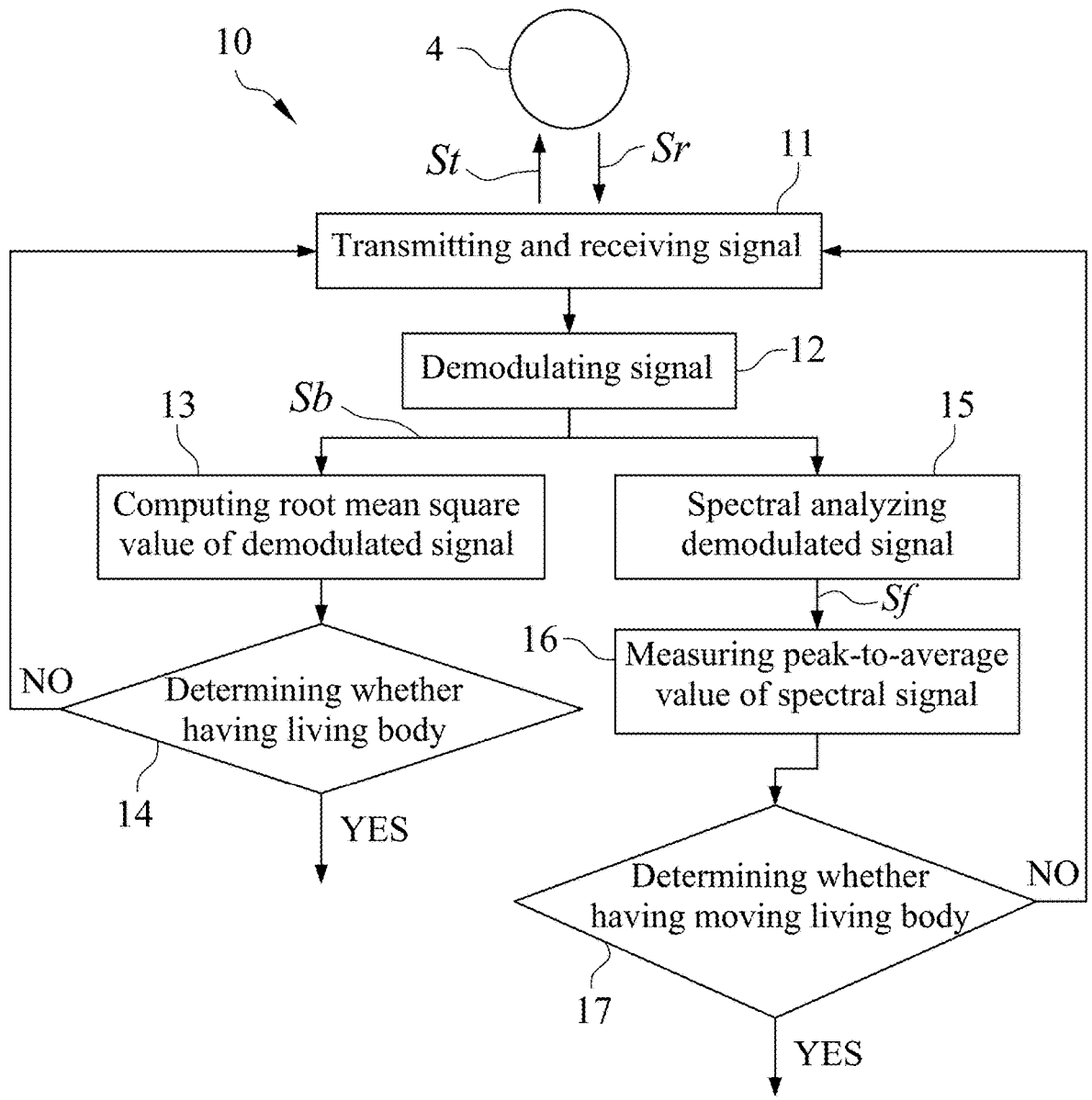
FIG. 1 is a flowchart illustrating a life detection method in accordance with a first embodiment of the present invention.
Figure 2:
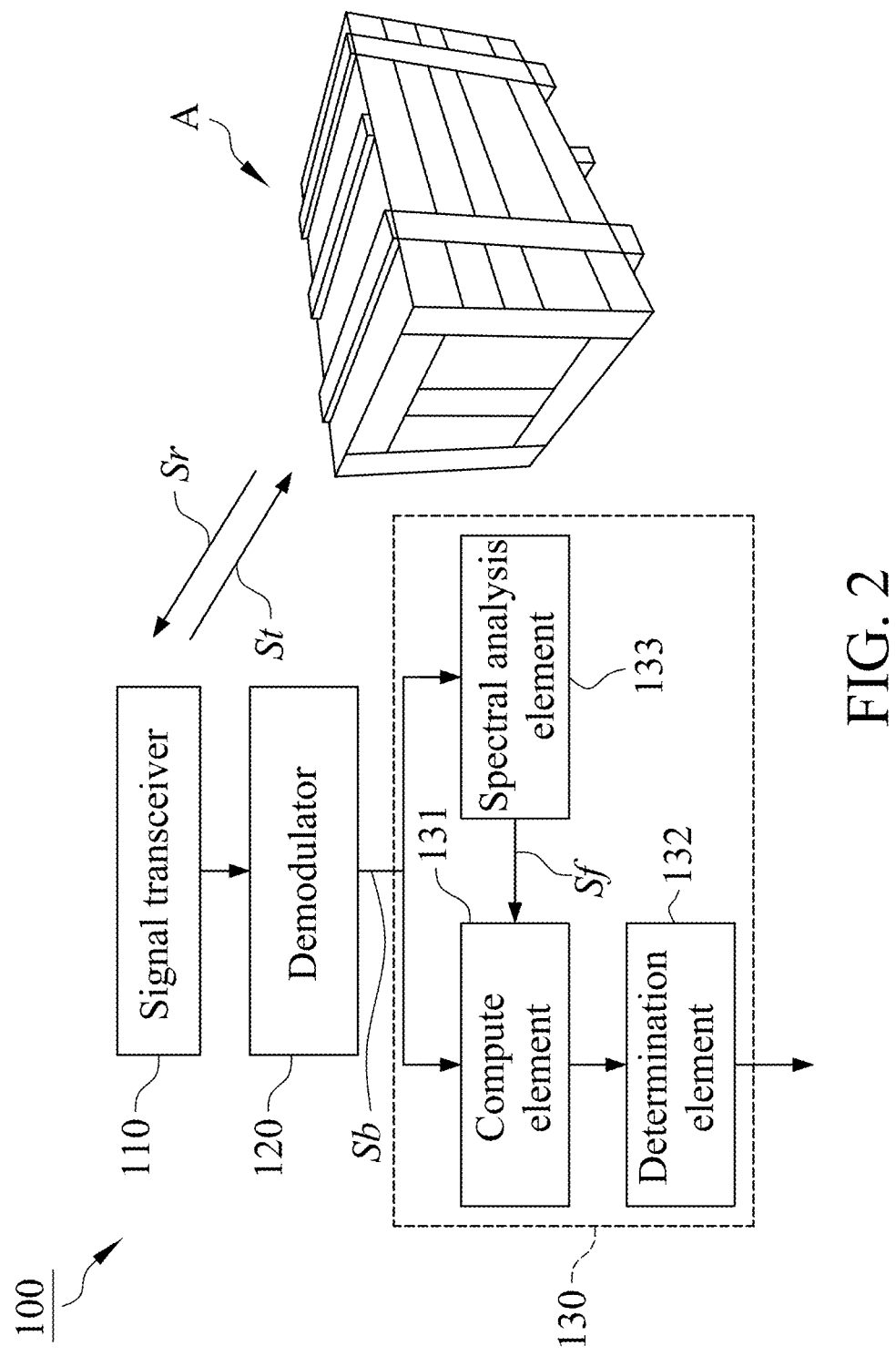
FIG. 2 is a functional block diagram illustrating a life detection radar in accordance with the first embodiment of the present invention.

With reference to FIGS. 1 and 2, a life detection method 10 practiced by a life detection radar 100 in accordance with a first embodiment of the present invention, wherein the life detection radar 100 may be continuous or pulse Doppler radar. The life detection method 10 includes a step 11 of transmitting and receiving signal, a step 12 of demodulating signal, a step 13 of computing root mean square value of demodulated signal, a step 14 of determining whether having living body, a step 15 of spectral analyzing demodulated signal, a step 16 of measuring peak-to-average value of spectral signal and a step 17 of determining whether having moving living body. In other embodiment, the life detection method 10 may only include the steps 11, 12, 13 and 14 to detect living body, not moving living body.

With reference to FIGS. 1 and 2, a signal transceiver 110 of the life detection radar 100 transmits a transmission signal St to an area A in the step 11. The area A may be an open space or a non-metallic container, such as a wood box shown in FIG. 2. Then the signal transceiver 110 receives a reflected signal Sr from the area A as a detection signal.

With reference to FIGS. 1 and 2, a demodulator 120 of the life detection radar 100 is coupled to the signal transceiver 110. The demodulator 120 receives and demodulates the detection signal to output a demodulated signal Sb in the step 12.

A signal processor 130 of the life detection radar 100 receives the demodulated signal Sb from the demodulator 120 in the step 13. In the first embodiment, the signal processor 130 includes a compute element 131 and a determination element 132 which are electrically connected to one another. The compute element 131 is electrically connected to the demodulator 120 for receiving the demodulated signal Sb and configured to compute a root mean square (RMS) value of the demodulated signal Sb.

In the step 14, the compute element 131 receives the RMS value of the demodulated signal Sb and the determination element 132 determines whether having a living body within the area A according to the RMS value and a RMS threshold value.

If there is a living body located in the area A, a relative motion of the living body with respect to the signal transceiver 110 may cause the Doppler Effect on the transmission signal St transmitted from the signal transceiver 110. Even the living body is almost still, any tiny movement (e.g. vital signs) may also causes the Doppler effect on the transmission signal St. The Doppler effect may contribute to phase shifts of the reflected signal Sr and the detection signal result from the body movements. As a result, the RMS value increment due to a larger amplitude fluctuation may be found in the demodulated signal Sb while a living body stays within the area A. In the first embodiment, the determination element 132 compares levels of the RMS value of the demodulated signal Sb and the RMS threshold value to determine whether having a living body in the area A. The determination element 132 determines a living body appear in the area A when the RMS value is higher than the RMS threshold value.

With reference to FIGS. 1 and 2, not only motionless body, the life detection method 10 in the first embodiment also can detect moving living body within the area A by the steps 15, 16 and 17. A spectral analysis element 133 of the life detection radar 100 is provided to analyze the demodulated signal Sb and output a spectral signal Sf in the step 15. While the demodulated signal Sb has phase shifts caused by body movement or vital signs, the spectral signal Sf also has higher level of frequency corresponding to the body movement or vital signs such that moving living body can be detected.

With reference to FIGS. 1 and 2, owing to the body movement usually corresponds with lower frequency range in the spectral signal Sf, the compute element 131 receives the spectral signal Sf, computes a peak value (dB) and a mean value (dB) of the spectral signal Sf within a frequency range and obtain a difference (dB) by subtracting the mean value (dB) from the peak value (dB) in the step 16. In the first embodiment, the frequency range is from 0 Hz to 100 Hz.

The determination element 132 is coupled to the compute element 131 for receiving the difference (dB) and determines whether there is a living body moving within the area A according to the difference (dB) and a threshold value (dB) in the step 17. The peak value (dB) may be significantly higher than the mean value (dB) in the spectral signal Sf while the living body is moving so that the determination element 132 can compare the difference (dB) and the threshold value (dB) to determine is there a moving living body within the area A or not. If the difference (dB) is higher than the threshold value (dB), the determination element 132 determines there is a moving living body within the area A. Additionally, a living body without movement in the area A also can be detected in the step 17.

Figure 3:
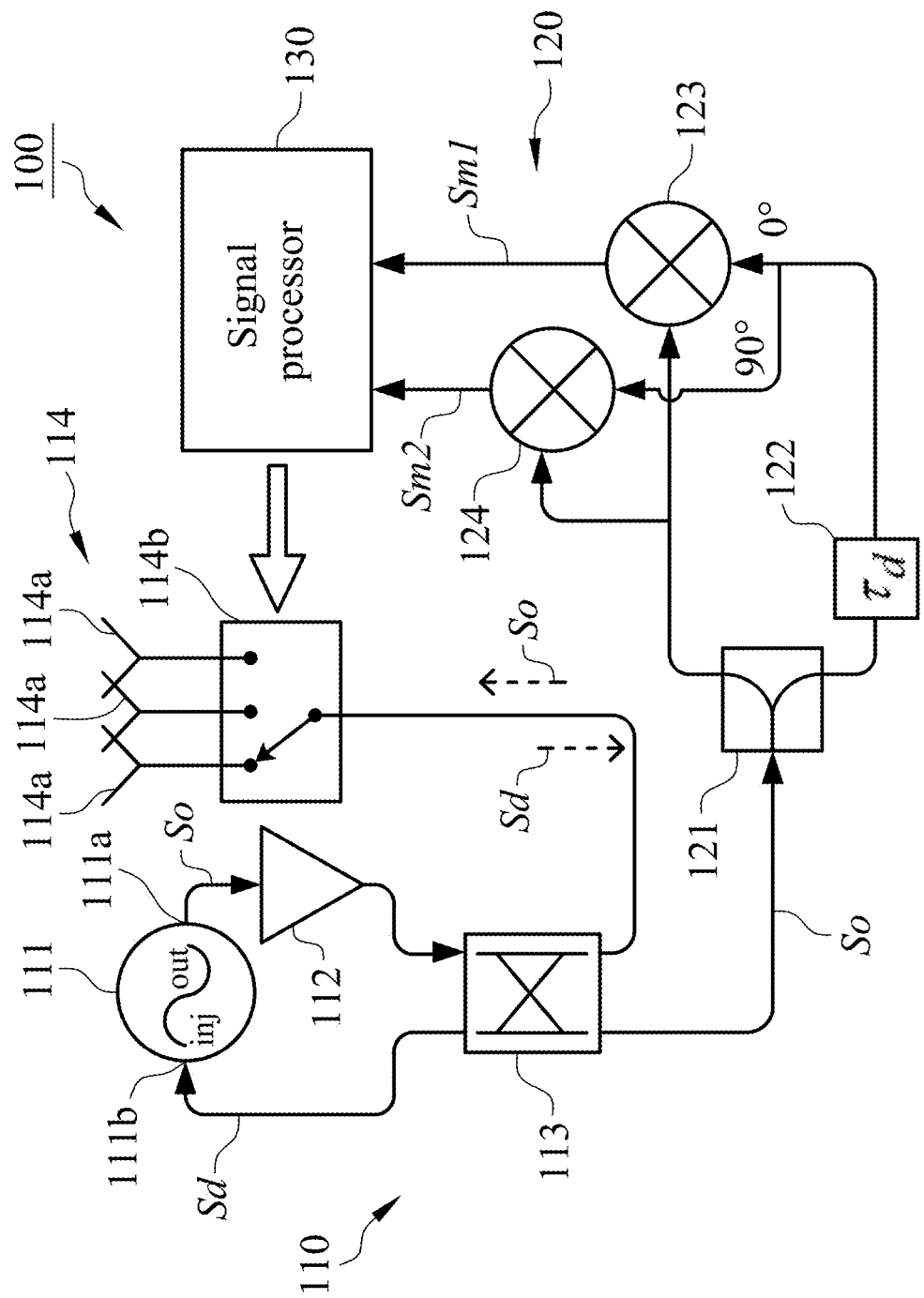
FIG. 3 is a circuit diagram illustrating a signal transceiver and a demodulator in accordance with a second embodiment of the present invention.

FIG. 3 represents a second embodiment of the present invention. In the second embodiment, the life detection radar 100 is a self-injection-locked radar and the signal transceiver 110 includes a self-injection-locked oscillator 111, a low-noise amplifier 112, a hybrid coupler 113 and an antenna element 114. The low-noise amplifier 112 is electrically connected to the self-injection-locked oscillator 111, the hybrid coupler 113 is electrically connected to the low-noise amplifier 112 and the self-injection-locked oscillator 111, the antenna element 114 and the demodulator 120 are electrically connected to the hybrid coupler 113. The self-injection-locked oscillator 111 includes an output port 111a and an injection port 111b, the self-injection-locked oscillator generates and outputs an oscillation signal So from its output port 111a to the low-noise amplifier 112. The low-noise amplifier 112 receives and amplifies the oscillation signal So and then the amplified oscillation signal So is delivered to the hybrid coupler 113. The hybrid coupler 113 couples the amplified oscillation signal So to the antenna element 114 and the demodulator 120 from the low-noise amplifier 112.

With reference to FIG. 3, the antenna element 114 includes a plurality of transceiver antennas 114a and a switch 114b. The switch 114b is electrically connected to the hybrid coupler 113 and coupled to the self-injection-locked oscillator 111 via the hybrid coupler 113 and the low-noise amplifier 112. The switch 114b receives the amplified oscillation signal So from the hybrid coupler 113. The transceiver antennas 114a are electrically connected to the switch 114b and the switch 114b switches one of them to be electrically connected to the hybrid coupler 113.

Accordingly, one of the transceiver antennas 114b coupled to the hybrid coupler 113 through the switch 114b is capable of receiving and transmitting the amplified oscillation signal So to the area A as the transmission signal St. In the second embodiment, the antenna element 114 includes three transceiver antennas 114a so that the three transceiver antennas 114a are able to transmit three transmission signals St to three different positions within the area A by switching of the switch 114b to expand the detection area of the life detection radar 100. The number of the transceiver antennas 114a in the antenna element 114 is not limited in the present invention and the antenna element 114 in other embodiment may have more or less than three transceiver antennas 114a.

The transmission signal St transmitted to the area A is reflected as the reflected signal Sr from the area A, the reflected signal Sr is received by the transceiver antenna 114a regarded as the detection signal Sd, and the detection signal Sd is delivered to the hybrid coupler 113 via the switch 114b and then coupled to the injection port 111b of the self-injection-locked oscillator 111 by the hybrid coupler 113. Because of the detection signal Sd, the self-injection-locked oscillator 111 operates in a self-injection-locked state to output the oscillation signal So having frequency proportional to the phase shift level in the detection signal Sd. The phase shift level of the detection signal Sd can be identified by demodulating the oscillation signal So. Further, the oscillation signal So from the self-injection-locked oscillator 111 is highly sensitive to tiny vibrations of living body and that is helpful for the signal processor 130 to determine whether having living body or moving living body.

With reference to FIG. 3, the demodulator 120 is a quadrature demodulator in the second embodiment and includes a power splitter 121, a delay element 122, a first mixer 123 and a second mixer 124. The power splitter 121 is electrically connected to the hybrid coupler 113 and configured to receive and divide the oscillation signal So coupled by the hybrid coupler 113 into two signals. One is delivered to the first mixer 123 and the second mixer 124 directly as local oscillation signals, and the other one is delivered to the first mixer 123 and the second mixer 124 via the delay element 122 and a quadrature power splitter (not shown) as signals having a phase difference of 90 degrees. The first mixer 123 receives and mix the signals as a first mixing signal Sm1, and the second mixer 124 receives and mix the signals as a second mixing signal Sm2.

Figure 4:
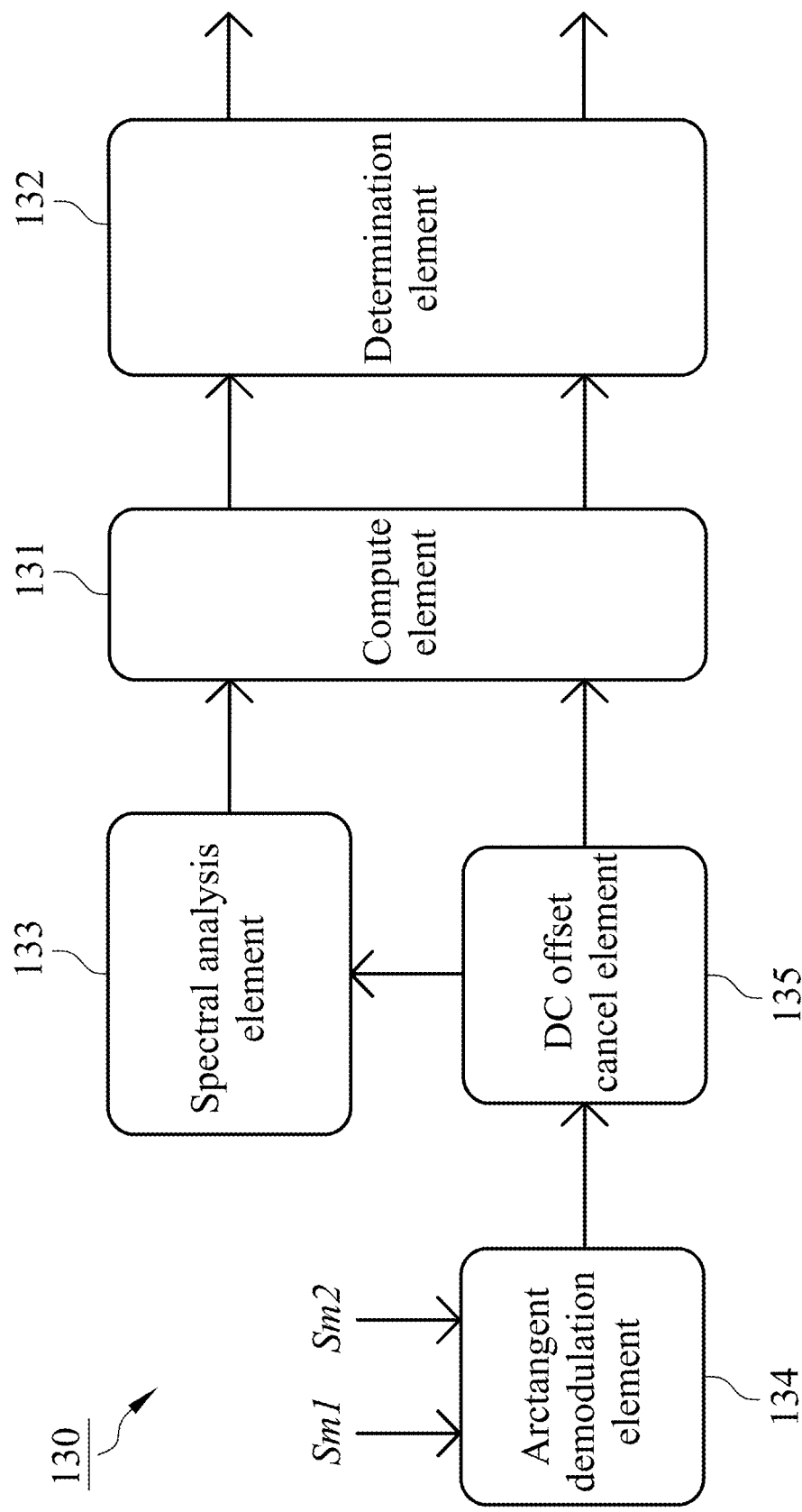
FIG. 4 is a functional block diagram illustrating a signal processor in accordance with the second embodiment of the present invention.

With reference to FIG. 4, the signal processor 130 in the second embodiment preferably further includes an arctangent demodulation element 134 and a DC offset cancel element 135. The arctangent demodulation element 134 receives and demodulates the first mixing signal Sm1 and the second mixing signal Sm2 through arctangent demodulation to output the demodulated signal. The DC offset cancel element 135 is electrically connected to the arctangent demodulation element 134 for receiving the demodulated signal and cancels the DC offset components in the demodulated signal to prevent surges in backend computation.

The present invention utilizes the compute element 131 to compute the RMS value of the demodulated signal Sb so that the determination element 132 can determine whether there is a living body within the area A according to the RMS value and the RMS threshold value. The life detection can be performed rapidly without influence from cargoes due to wireless means and simple computation.

The scope of the present invention is only limited by the following claims. Any alternation and modification without departing from the scope and spirit of the present invention will become apparent to those skilled in the art.

What is claimed is:

1. A life detection method, comprising:
    transmitting a transmission signal to an area and receiving a reflected signal from the area as a detection signal by using a signal transceiver;
    receiving and demodulating the detection signal to output a demodulated signal by using a demodulator coupled to the signal transceiver;
    receiving the demodulated signal and computing a root mean square (RMS) value of the demodulated signal by using a compute element coupled to the demodulator; and
    receiving the RMS value of the demodulated signal and determining whether having a living body within the area according to the RMS value and a RMS threshold value by using a determination element coupled to the compute element.

2. The life detection method in accordance with claim 1, wherein the determination element is configured to compare the RMS value of the demodulated signal and the RMS threshold value, and the determination element determines there having the living body within the area when the RMS value is higher than the RMS threshold value.

3. The life detection method in accordance with claim 1, wherein the signal transceiver includes a self-injection-locked oscillator and an antenna element, the self-injection-locked oscillator is configured to generate a oscillation signal, the antenna element is configured to receive the oscillation signal, transmit the oscillation signal to the area as the transmission signal and receive the reflected signal as the detection signal, and the detection signal is configured to be injected into the self-injection-locked oscillator such that the self-injection-locked oscillator operates in a self-injection-locked state.

4. The life detection method in accordance with claim 3, wherein the antenna element includes a plurality of transceiver antennas and a switch, the transceiver antennas are electrically connected to the switch, the switch is coupled to the self-injection-locked oscillator and configured to switch one of the transceiver antennas to be coupled to the self-injection-locked oscillator.

5. The life detection method in accordance with claim 3, wherein the signal transceiver further includes a low-noise amplifier and a hybrid coupler, the low-noise amplifier is electrically connected to a output port of the self-injection-locked oscillator and configured to amplify the oscillation signal, the hybrid coupler is electrically connected to the low-noise amplifier, an injection port of the self-injection-locked oscillator and the compute element, and the hybrid coupler is configured to couple the oscillation signal to the antenna element and the compute element and configured to couple the detection signal to the injection port of the self-injection-locked oscillator.

6. The life detection method in accordance with claim 1, wherein a spectral analysis element is configured to analyze the demodulated signal and output a spectral signal, the compute element is configured to receive the spectral signal, compute a peak value (dB) and a mean value (dB) of the spectral signal within a frequency range and obtain a difference (dB) between the peak value (dB) and the mean value (dB).

7. The life detection method in accordance with claim 6, wherein the determination element is coupled to the compute element and configured to receive the difference (dB) and determine whether having a moving living body within the area according to the difference (dB) and a threshold value (dB).

8. The life detection method in accordance with claim 7, wherein the determination element is configured to compare the difference (dB) and the threshold value (dB), and when the difference (dB) is higher than the threshold value (dB), the determination element determines there having the moving living body within the area.

9. A life detection radar, comprising:
    a signal transceiver including a self-injection-locked oscillator and an antenna element, the antenna element is coupled to the self-injection-locked oscillator and configured to receive a oscillation signal, transmit the oscillation signal to an area as a transmission signal and receive a reflected signal from the area as a detection signal, the detection signal is configured to be injected into the self-injection-locked oscillator such that the self-injection-locked oscillator operates in a self-injection-locked state;
    a demodulator electrically connected to the signal transceiver and configured to receive and demodulate the oscillation signal as a demodulated signal; and
    a signal processor electrically connected to the demodulator and configured to receive the demodulated signal, the signal processor includes a compute element and a determination element, the compute element is configured to compute a root mean square (RMS) value of the demodulated signal, the determination element is coupled to the compute element and configured to receive the RMS value and determine whether having a living body within the area according to the RMS value and a RMS threshold value.

10. The life detection radar in accordance with claim 9, wherein the signal processor further includes a spectral analysis element configured to analyze the demodulated signal to output a spectral signal, the compute element is configured to receive the spectral signal, compute a peak value (dB) and a mean value (dB) of the spectral signal within a frequency range and obtain a difference (dB) between the peak value (dB) and the mean value (dB), the determination element is coupled to the compute element and configured to receive the difference (dB) and determine whether having a moving living body within the area according to the difference (dB) and a threshold value (dB).

* * * * *